(12) United States Patent
Morris et al.

(10) Patent No.: US 9,283,550 B2
(45) Date of Patent: Mar. 15, 2016

(54) BIFUNCTIONAL MATERIAL FOR NITRIC OXIDE STORAGE AND PRODUCTION AND USE THEREOF IN THERAPY

(75) Inventors: Russel Edward Morris, St. Andrews (GB); Ian L. Megson, Inverness (GB)

(73) Assignees: University Court of the University of St Andrews (GB); University Court of the University of Edinburgh (GB)

( * ) Notice: Subject to any disclaimer, the term of this patent is extended or adjusted under 35 U.S.C. 154(b) by 1476 days.

(21) Appl. No.: 12/515,474

(22) PCT Filed: Nov. 19, 2007

(86) PCT No.: PCT/GB2007/004367
§ 371 (c)(1),
(2), (4) Date: Dec. 1, 2009

(87) PCT Pub. No.: WO2008/062160
PCT Pub. Date: May 29, 2008

(65) Prior Publication Data
US 2010/0112095 A1    May 6, 2010

(30) Foreign Application Priority Data

Nov. 25, 2006 (GB) .................................. 0623531.1

(51) Int. Cl.
| | |
|---|---|
| A61L 27/20 | (2006.01) |
| A61L 27/34 | (2006.01) |
| A61L 27/50 | (2006.01) |
| A61L 27/52 | (2006.01) |
| A61L 33/00 | (2006.01) |
| B01J 29/072 | (2006.01) |
| A01N 59/00 | (2006.01) |
| A61K 47/02 | (2006.01) |
| A01N 25/08 | (2006.01) |
| A61K 8/19 | (2006.01) |
| A61K 8/26 | (2006.01) |
| A61K 33/00 | (2006.01) |
| A61K 33/06 | (2006.01) |
| A61K 33/34 | (2006.01) |
| A61K 45/06 | (2006.01) |
| A61L 15/44 | (2006.01) |
| A61L 29/16 | (2006.01) |
| A61L 31/16 | (2006.01) |
| A61Q 19/00 | (2006.01) |
| B01J 20/02 | (2006.01) |
| B01J 20/06 | (2006.01) |
| B01J 20/18 | (2006.01) |
| B01J 20/32 | (2006.01) |
| A61K 9/14 | (2006.01) |
| A01N 25/26 | (2006.01) |
| B01J 23/72 | (2006.01) |
| B01J 29/14 | (2006.01) |
| B01J 29/46 | (2006.01) |

(52) U.S. Cl.
CPC ............... *B01J 29/072* (2013.01); *A01N 25/08* (2013.01); *A01N 59/00* (2013.01); *A61K 8/19* (2013.01); *A61K 8/26* (2013.01); *A61K 33/00* (2013.01); *A61K 33/06* (2013.01); *A61K 33/34* (2013.01); *A61K 45/06* (2013.01); *A61K 47/02* (2013.01); *A61L 15/44* (2013.01); *A61L 27/20* (2013.01); *A61L 27/34* (2013.01); *A61L 27/507* (2013.01); *A61L 27/52* (2013.01); *A61L 29/16* (2013.01); *A61L 31/16* (2013.01); *A61L 33/0011* (2013.01); *A61L 33/0064* (2013.01); *A61Q 19/00* (2013.01); *B01J 20/02* (2013.01); *B01J 20/0237* (2013.01); *B01J 20/06* (2013.01); *B01J 20/18* (2013.01); *B01J 20/186* (2013.01); *B01J 20/3234* (2013.01); *A01N 25/26* (2013.01); *A61K 9/143* (2013.01); *A61L 2300/114* (2013.01); *B01J 23/72* (2013.01); *B01J 29/143* (2013.01); *B01J 29/46* (2013.01); *B01J 2220/42* (2013.01)

(58) Field of Classification Search
None
See application file for complete search history.

(56) References Cited

U.S. PATENT DOCUMENTS

2004/0224868 A1* 11/2004 Meyerhoff et al. ............ 510/320

FOREIGN PATENT DOCUMENTS

| WO | WO 02/056904 A1 | 7/2002 |
| WO | WO 2005/003032 A1 | 1/2005 |

OTHER PUBLICATIONS

Zhang et al., NO Adsorbability of Metal Ion-Exchanged Molecular Sieve, Chemical Journal of Chinese Universities (1997), vol. 18, No. 12, pp. 1-6.*
Remington's Pharmaceutical Sciences (17th Ed. 1985), p. 1032.*
Jewell et al., Industrial Wastewater Treatment Using South African Natural Zeolite, Clinoptilolite, Water Research Commission (2002).*

(Continued)

*Primary Examiner* — Abigail Fisher
*Assistant Examiner* — Frank Choi
(74) *Attorney, Agent, or Firm* — Susan T. Evans; McDermott Will & Emery LLP

(57) ABSTRACT

The present invention relates to a bifunctional material which comprises copper and which is capable of storing nitric oxide (NO), as well as catalytically producing nitric oxide from a suitable precursor. The material typically includes a zeolite and the copper may be part of, or separate from the zeolite. In this manner the material may include a single bifunctional material; that is, a material which is capable of both storing NO and catalytically producing NO, such as Cu-MFI or Cu-X. Alternatively the material may include at least two components, a first component to store NO, such as a zeolite Zn-LTA, and a further component including Cu(I), such as $Cu_2O$, to catalytically produce NO from a suitable precursor. The bifunctional material may be used in a pharmaceutical, neutraceutical or cosmetic preparation, or comprised in a medical article, a cosmetic and/or personal hygiene product.

19 Claims, 4 Drawing Sheets

(56) References Cited

OTHER PUBLICATIONS

Oh et al. "Catalytic generation of nitric oxide from nitrite at the interface of polymeric films doped with lipophilic (Cu(II)-complex: a potential route to the preparation of thromboresistant coatings", *Biomaterials* 25:283-293 (2004).

International Search Report corresponding to International Application No. PCT/GB2007/004367 mailed Feb. 13, 2008.

Yahiro, H., Iwamoto, M., "Copper ion-exchanged zeolite catalysis in deNO$_x$ reaction", *Applied Catalysis A: General* 222 (2001) 163-181.

* cited by examiner

BIFUNCTIONAL MATERIAL FOR NITRIC OXIDE STORAGE AND PRODUCTION AND USE THEREOF IN THERAPY

CROSS-REFERENCE TO RELATED APPLICATIONS

The present application is a 35 U.S.C. §371 national phase application of PCT International Application No. PCT/GB2007/004367, having an international filing date of Nov. 19, 2007, claiming priority to Great Britain Patent Application No. 0623531.1, filed Nov. 25, 2006. The disclosures of each application are incorporated herein by reference in their entireties. The above PCT International Application was published in the English language as International Publication No. WO 2008/062160A1.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION BY REFERENCE OF MATERIAL SUBMITTED ON A COMPACT DISC

Not applicable.

BACKGROUND OF THE INVENTION

1. Field of the Invention

The present invention relates to a bifunctional material comprising a zeolite which is capable of releasably absorbing nitric oxide and producing nitric oxide from a suitable precursor molecule.

2. Background Art

Storage of gases in tailored porous materials is an extremely important technology with great potential for impact in a wide variety of applications, from energy storage and environmental remediation to biological/medical devices. The gases of interest encompass hydrogen (N. L. Rosi, J. Eckert, M. Eddaoudi, D. T. Vodak, J. Kim, M. O'Keeffe, O. M. Yaghi Science, 300, 1127, (2003)), various different hydrocarbons (M. Eddaoudi, J. Kim, N. Rosi, D. T. Vodak, J. Wachter, M. O'Keeffe, O. M. Yaghi, Science, 295, 469, (2002); R. Matsuda, R, Kitaura, S. Kitagawa, Y. Kubota, R. V. Belosludov, T. C. Kobayashi, H. Sakamoto, T. Chiba, M. Takata, Y. Kawazoe, Y. Mita, Nature 436, 238, (2005)), carbon dioxide (A. R. Millward, O. M. Yaghi, J. Am Chem Soc. 127 17998 (2005)) and nitric oxide (Keefer, L. K. Nature Materials, 2, 357 (2003); P. S. Wheatley, A. R. Butler, M. S. Crane, B. Xiao, A. G Rossi, I. L. Megson R. E. Morris, J. Am Chem Soc. 2006, 128, 502-509). A major drawback of gas storage materials is the finite reservoir of gas that is available—eventually even the highest capacity materials will run out of the stored gas, no matter how slowly it is delivered for use. For some applications, where recharging the material with the required gas is relatively easy or if the material is completely replaced with a new gas loaded sample, this may not be of too much concern. However, where the gas storage material needs to be in place for a long time, the limited lifetime of stored gas may be a significant handicap. A prime example of a situation where this could be vitally important is the use of nitric oxide (NO) releasing materials in medical devices or implants that need to remain in situ for days, months or even years. In such cases, NO release needs to last an equally long time to ensure that the beneficial effects continue. With simple gas storage materials, this is unlikely to be possible.

NO is an extremely important signalling molecule in mammalian biology, and there is increasing evidence that exogenously applied NO is beneficial in a number of areas, including the prevention of thrombosis, the promotion of wound healing and anti-microbial therapies.

The present inventors have recently showed how zeolites (porous alumino silicate materials) can be used to store and deliver NO in biologically important amounts (P. S. Wheatley, A. R. Butler, M. S. Crane, B. Xiao, A. G Rossi, I. L. Megson R. E. Morris, J. Am Chem Soc. 2006, 128, 502-509)). This work showed how, zeolites irreversibly adsorb large amounts of NO, which is only released on the action of a trigger such as exposure to moisture. The storage lifetime of NO in zeolites is long term (no loss of NO delivery even after 1 year's storage) and can be tailored for a particular application by altering the composition of the zeolite or by blending the zeolites with appropriate polymer matrices. The use of zeolites as water softeners in detergent powder formulations also means that their toxicology is relatively well studied, at least in terms of topical exposure.

However, for biological applications it is not the storage capacity of the material that is the most important feature, but the match between the rate and duration of delivery and that required by the target application. NO is produced by the endothelial cells that line normal healthy blood vessels at a rate that has been estimated to be ~1 pmol $min^{-1}$ $mm^{-2}$ and this mediates a number of vital functions including vasodilatation (Furchgott, R. F.; Zawadzki, J. V., Nature 1980, 288, 373; Palmer, R. M. J.; Ferrige, A. G.; Moncada, S. Nature 1987 327, 524), prevention of vascular smooth muscle growth and inhibition of platelet (Radomski, M. W.; Palmer, R. M. J.; Moncada, S., Lancet 1987, 2, 1057) and inflammatory cell (Bath, P. M. W.; Hassall, D. G.; Gladwin. A. M.; Palmer, R. M. J.; Martin, J. F., Arterioscler. Thromb. 1991, 11, 254; Kubes, P.; Suzuki, M.; Granger, D. N., Proc. Natl Acad. Sci, USA. 1991, 87, 5193) activation and adhesion. To mimic the action of endothelial NO on the surface of a medical implant such as a stent requires a relatively low rate of NO delivery over a considerable period of time. However, NO also has an anti-microbial effect, and larger amounts of NO prevent biofilm formation and can be used to kill many different organisms, even resistant bacterial strains such as MRSA (A. GhaVari, C. C. Miller, B. McMullin, A. Ghahary, Nitric Oxide 14, 21, (2006); see the international zeolite association website www.iza-online.org for details of how the codes relate to the framework structures of the zeolites). Since many failures of medical implants can be traced back to infection (B. J. Nablo, H. L. Prichard, R. D. Butler, B. Klitzman, M H. Schoenfisch, Biomaterials 26, 6984 (2005)) this anti-microbial action of NO is also very desirable, and could be performed by a short burst (minutes to hours) of NO on first use of the implant. A material that delivers a burst of NO followed by a steady release of NO at a lower level maybe the optimum behaviour for medical applications of this type. It is expected that it will be impossible to obtain such a release profile from simple stored NO and as such there is a requirement for novel materials designed to address the above problems.

It is therefore amongst the objects of the present invention to obviate and/or mitigate at least one of the aforementioned disadvantages.

It is a further object of the present invention to provide a bifunctional product which is capable of storing NO and also producing NO from a precursor material.

BRIEF SUMMARY OF THE INVENTION

In a first aspect there is provided a bifunctional material which comprises copper and which is capable of storing nitric oxide (NO), as well as catalytically producing nitric oxide from a suitable precursor.

The material typically comprises a zeolite and the copper may be part of, or separate from the zeolite. In this manner, the material may comprise a single bifunctional material; that is, a material which is capable of both storing NO and catalytically producing NO. Alternatively the material may comprise at least two components, a first component to store NO and a further component to catalytically produce NO from a suitable precursor.

In one embodiment the material comprises a zeolite comprising copper, such as Cu(II) which is capable of irreversibly releasably storing NO and producing NO catalytically from a suitable precursor.

In a second embodiment, the material comprises a final zeolite component which is capable of irreversibly releasably storing NO and a second Cu(I) comprising component, such as $Cu_2O$ which can be used to catalytically produce NO from a suitable precursor.

For the avoidance of doubt, reference to the material "being capable of irreversibly releasably storing" is understood to relate to the material in the absence of or when storing NO.

It is particularly preferred that the materials of the present invention are intended for use in medical applications including surgery and therapy, as well as in cosmetic application.

Thus, according to a further aspect of the present invention there is provided a pharmaceutical, neutraceutical or cosmetic preparation comprising a bifunctional material as described herein comprising irreversibly releasably adsorbed nitric oxide and being capable of catalytically producing nitric oxide from a suitable precursor molecule together with a pharmaceutical/neutraceutical/cosmetic carrier therefor.

The present invention also provides the use of a bifunctional material comprising irreversibly releasably adsorbed NO and being capable of catalytically producing NO from a suitable precursor molecule in the preparation of a medicament for use in the treatment or prophylaxis of disease.

Diseases or medical conditions which may be treated include infections of the skin, including dermatophyte fungi, leishmaniasis, molluscum and papilloma virus, and *mycobacterium* infections, including those associated with chronic circulatory disorders (e.g. diabetic foot ulcers). Further uses include therapeutic applications in anti-neoplastic activities, immune response modification, treatment of Raynaud's disease, wound healing and skin pigment modification. Yet further uses include treatment of restenonsis, psoriasis and eczema, and skin cancer (melanoma). Therapies for other bacterial problems include the reduction of severe foot or body odour problems, and in the treatment of Methicillin Resistant *Staphylococcus Aureus* infections.

An area of considerable potential with respect to the invention is the coating of or incorporation into medical devices that contact blood. Such items include medical instruments, cannulae (arterial and venous), catheters (e.g. urinary and those used in cardiology and surgical procedures), stents (e.g. coronary), shunts, prosthetic grafts and extracorporeal tubing, filters and associated components used in, for example, bypass surgery, renal dialysis and constant glucose monitoring equipment and insulin delivery pumps used in diabetes.

According to a further aspect of the present invention there is provided a medical article comprising a material according to the present invention which comprises irreversibly releasable absorbed nitric oxide and being capable of catalytically producing nitric oxide from a suitable precursor molecule.

The material of the medical article may be provided without NO loaded therein to allow loading with NO prior to use and/or storage of the medical device ready for subsequent use.

Alternatively, the material of the medical article may be provided as a zeolite material comprising releasably adsorbed NO.

Suitable medical articles for use in the present invention include stents, shunts, catheters, cannulae, extra-corporeal tubing, filters, wound dressings, bandages, self-adhesive plasters and patches.

The beneficial properties of NO may be advantageously employed in cosmetic and personal hygiene applications.

According to a further aspect of the present invention, there is provided use of a bifunctional material comprising releasably adsorbed NO and being capable of catalytically producing NO from a suitable precursor molecule in cosmetic and/or personal hygiene applications.

For example the materials of the present invention may be used in cosmetic preparations; deodorants; skin preparations such as anti-aging skin preparations and preparations applied before, during or after hair removal by shaving or by application of depilatory preparations; hair preparations; depilatory preparations and the like.

Accordingly, the present invention also provides, a cosmetic and/or personal hygiene product comprising a material according to the present invention.

The present invention also provides, as a further aspect, a method of releasing and producing NO comprising the steps of (i) providing a material comprising irreversibly releasably adsorbed nitric oxide and being capable of catalytically producing NO from a suitable precursor molecule;

(ii) contacting said material with a medium into which said NO is to be provided, by release of the stored NO and by catalytic production of NO;

Such release of NO is preferably achieved in a controlled manner, for example, by providing a suitable material with an established controlled release profile. For example, the material may provide an initial stored burst of NO from the releasably stored NO, followed by a prolonged production of NO.

The medium into which the NO is to be released may be simply air surrounding the material or may be, for example, an aqueous medium.

The release may be performed either inside an animal body, topically to an animal body or in non-body applications such as release into cell cultures.

The release may be performed at any suitable temperature, however room or body temperature is preferred.

The method of releasing NO may be applied to the treatment of humans or animals and accordingly the present invention further provides as a further aspect a method of treatment or prophylaxis of an individual in need thereof comprising providing a material comprising releasably adsorbed nitric oxide and being capable of catalytically producing nitric oxide from a suitable precursor molecule and contacting said zeolite with said individual.

The present invention will now be further described by way of example and with reference to the figures which show the following:

DETAILED DESCRIPTION OF THE INVENTION

Figure 1:
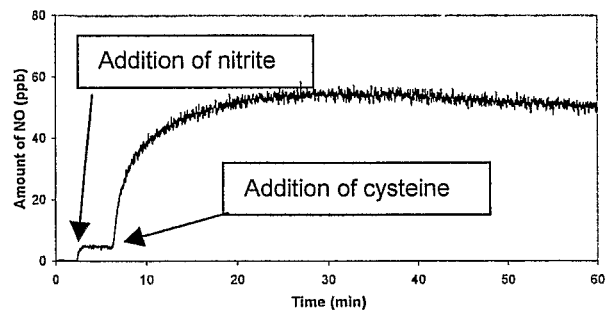
FIG. 1 shows the addition of nitrite solution (at 2.5 mins) to a buffered solution in which solid Cu-MFI (also known as Cu-ZSM-5) has been dispersed leads to a significant amount of NO being detected. Addition of a reducing agent (cysteine, at 6 mins) leads to ten-fold increase in the amount of NO detected. 34 μmol of NO were produced per gram of Cu-MFI with a conversion of 1.9% for 60 minutes.

In a first aspect there is provided a bifunctional material which comprises copper and which is capable of storing nitric oxide (NO), as well as catalytically producing nitric oxide from a suitable precursor.

The material typically comprises a zeolite and the copper may be part of, or separate from the zeolite. In this manner, the material may comprise a single bifunctional material; that is, a material which is capable of both storing NO and catalytically producing NO. Alternatively the material may comprise at least two components, a first component to store NO and a further component to catalytically produce NO from a suitable precursor.

In one embodiment the material comprises a zeolite comprising copper, such as Cu(II) which is capable of irreversibly releasably storing NO and producing NO catalytically from a suitable precursor.

In a second embodiment, the material comprises a final zeolite component which is capable of irreversibly releasably storing NO and a second Cu(I) comprising component, such as $Cu_2O$ which can be used to catalytically produce NO from a suitable precursor.

For the avoidance of doubt, reference to the material "being capable of irreversibly releasably storing" is understood to relate to the material in the absence of or when storing NO.

Zeolites are a class of aluminosilicate materials (both natural and synthetic) that contain pores and channels of dimensions that allow small molecules or ions to be adsorbed onto the internal surfaces of the material. The general formula of the zeolite framework is $Al_y S_{1-y} O_4^{y-}$, and it is clear that for every aluminium in the framework, one negative charge is introduced that must be balanced by an extra-framework cation. These cations can be inorganic or organic in nature, and can be exchanged using standard ion exchange processes.

Dehydrated 'as synthesised' and ion exchanged zeolites with the compositions $[(M1^{n+})_{x/n}(M2^{p+})_{y/p}][Al_z Si_{2-z} O_4]$ where x can range from zero to nz, and y from zero to pz subject to the condition that $x/n + y/p = z$ are preferred, wherein;

M1 and M2 are extra-framework metal cation of elements, Li, Na, K, Ca, Mg, Fe, Cu, Mn, V, Ti, Ru, Rh, Co, Ni, Zn and Ag.

For biological, medical and/or cosmetic applications (see herein below), preferred metal cations are those which are deemed toxicologically acceptable for such uses, e.g. those metals which are considered to have acceptable/limited toxicity, particularly when presented in the framework material, although such considerations will depend on the circumstances of the use and may be determined by the skilled practitioner as appropriate.

The zeolite frameworks may comprise or contain additional entities to those described above, for example, further metal or other positively charged ions, or other anionic species. Further anions may include halogens, e.g. $Cl^-$, $F^-$, $Br^-$ or $I^-$ or other anions, e.g. $OH^-$ or $SO_4^-$.

The zeolite frameworks may in particular include species/molecules, within guest sites, such as pores or channels, formed in the framework. Such species may be for example water, solvent or other molecules e.g. derived from the components used in the manufacture of the framework.

Prior to NO adsorption (loading), the zeolite frameworks for use in the present invention may (or may not) be fully or partially activated. The term "activated" refers to the zeolite framework being presented in a state in which NO may be adsorbed at least "irreversibly" to some degree. The frameworks may inherently allow the NO to be adsorbed irreversibly (at least to some extent), in which case, activation may not be required, or activation may be used to increase the amount of NO which may be adsorbed.

If required, activation generally involves the removal of guest molecules/species from the interior of the pores and/or channels of the framework to allow the NO to be adsorbed into the zeolite framework. The guest molecules/species may be coordinated to the metals in the zeolite, and the activation of the framework materials may include removal of such coordinated molecules/species. The guest molecules/species may be nucleophiles or water.

For example, the zeolite framework may become coordinatively activated, wherein the activated zeolite framework includes a site available for coordination on some or all of the metal cations that form part of the framework itself. The available metal cations are thus available to strongly ("irreversibly") bind NO through coordination of the gas to the metal cation(s).

The term "irreversibly releasably store" NO refers to NO which is bound to the material strongly and is not substantially desorbed from the material once the nitric oxide-containing atmosphere used to load the material with the gas is removed, in particular, at a reduced pressure. Without wishing to be bound by theory, this irreversible adsorption is understood to be a chemisorption process (i.e. there is a chemical bond formed between the nitric oxide and the zeolite framework material). The presence of irreversibly adsorbed NO (or any other species) is indicated by a strong hysteresis between the adsorption and desorption arms of the adsorption/desorption isotherm.

In contrast, reversibly adsorbed NO is weakly bound to the material and desorbs once the NO-containing atmosphere used to load the material with the gas is removed. The NO adsorbed by this mechanism is thereby termed "reversibly" is weakly bound NO.

Activation may be achieved chemically, optionally followed by other non-chemical means or vice versa.

Chemical activation tends to remove the unwanted guest molecules from the framework by chemical displacement of the guest molecules by the molecules of the chosen activating chemical species. The NO itself may be used to displace the unwanted guest molecules.

The other, non-chemical, means for activation may include heating the zeolite framework at ambient (e.g. atmospheric) or reduced pressure. Subjecting the framework material to reduced pressure in absence of heat may also be used. Methods include, for example, placing the framework under vacuum at elevated temperatures. Preferably, zeolites are activated thermally in this manner.

Other, non-chemical means for activation include exposing the zeolite framework to electromagnetic radiation, e.g. ultraviolet light.

Alternatively, the framework is subjected to a chemical activation procedure followed by heating. Such method advantageously may take advantage of a step-wise activation procedure whereby guest molecules/species are preferentially displaced by a different chemical entity which becomes a guest molecule/species, which is then removed from the framework under reduced pressure and/or heating the framework material.

Chemical activation may be achieved using a chemical treatment method such as exposure of the framework material to a desired chemical or a mixture of chemicals.

Examples of suitable chemicals include solvents such as acetonitrile ($CH_3CN$), dimethylformamide (DMF), ethanol (EtOH) or methanol (MeOH).

Typical pressures, preferably reduced pressures, which may be used for activation include a pressure less than atmospheric pressure, e.g. less than 1 bar, such as from about $1 \times 10^{-4}$ mbar to about 1 bar.

Typical temperatures, preferably elevated temperatures, which may be used for activation include a temperature up to about 600° C., preferably about 300 to 600° C. for optimum activation and lower temperatures (e.g. 200 to 300° C.) for partial activation.

The guest molecules may comprise water, in which case, activation of the framework includes full or partial dehydration of the framework material, to remove water. Other guest molecules such as residual solvent or gases may also be removed from the zeolite framework by the activation methods described herein.

The activation of the zeolite frameworks may also involve a change in structure of the framework to enable nitric oxide to be adsorbed irreversibly.

The resulting zeolite framework may then be exposed to nitric oxide to load the zeolite.

Typically, the NO loading is performed at a temperature of from −100° C. to 50° C.

The loading of NO may be performed with pure NO, substantially pure NO or with a mixture of NO and a carrier gas such as an inert gas, for example helium, argon or other inert gas including mixtures thereof.

The loading is typically performed at or above a pressure equal to atmospheric pressure, for example from atmospheric pressure up to a pressure of about 10 bar. Atmospheric pressure is generally understood to mean a pressure of about 1 bar.

The NO loaded zeolite frameworks may be sealed inside airtight packaging for storage and transport purposes.

The airtight packaging may conveniently contain a dry atmosphere under which the zeolite framework is sealed.

Upon exposure of the NO loaded zeolite framework to a suitable nucleophile, for example an aqueous environment such as water or blood, the NO is displaced from the metal complex inside the zeolite framework resulting in release of NO gas into the aqueous environment.

Thus, the irreversibly adsorbed NO may be considered to be releasably adsorbed NO when conditions under which its release is triggered are applied.

The release of the irreversibly adsorbed/bound NO may be triggered by the action of another species. e.g. one which preferentially becomes the guest in the zeolite framework, for example, displaces and takes the place of the NO at the coordination sphere of the metal cation in the zeolite framework. Such species include, for example, nucleophile species, and the method of release may comprise using a nucleophile-containing medium such as moist gas or an aqueous medium/solution, or by other means such as subjecting the nitric oxide-containing material to an elevated temperature or exposure to electromagnetic radiation, e.g. ultraviolet light.

The NO loaded material may be subjected to one or more these methods to render the irreversibly bound nitric oxide releasable, prior to subjecting the material to conditions to actually release the irreversibly bound nitric oxide.

The NO may be released from the NO loaded zeolite when placed in air, e.g. moist air.

For certain embodiments of the invention described herein the preferred extraframework cation is copper, either in its +1 or +2 oxidation states (also known as Cu(I) and Cu(II)). This can be present as the only extraframework cation or as a mixture with others.

The choice of particular zeolite structure will affect the properties of the material because of their different ion exchange capacities etc. Preferred frameworks are those with the three letter framework codes LTA, FAU, MFI, MOR, FER etc. The three letter codes [t] describe the framework architecture of the zeolites (i.e. their structure) but not the composition of the zeolite, which can vary quite widely according to the formula given above. The three letter codes have no other meaning than as a naming system. More details of preferred zeolite materials and their loading can be found in WO 2005/003032.

For use as a bifunctional material that both releasably stores and catalytically produces NO the zeolites may be dehydrated or partially dehydrated and then loaded with NO before use (for example WO2005/003032). For use just to catalytically produce NO, the zeolite can be used in its hydrated or dehydrated form without loading with NO.

Suitable copper (I) comprising materials include oxide materials such as $Cu_2O$. The class of material can also include copper (I) containing zeolites. These materials can be used in any suitable form, although high surface area solids (e.g. porous or nanoparticulate morphologies may be preferred).

Copper (II) comprising materials (such as the zeolites) may require a reductant (to ensure there is at least some copper (I) formed in situ). The reductant can be any compound that can reduce Cu(II) to Cu(I), and may be present naturally at the site of use of the material or prepared and added separately. Examples of such compounds include ascorbic acid and cysteine. Alternatively, Cu(I) may be formed in situ during the activation process, for example during the thermal activation of a copper (II) containing material.

The precursors used to catalytically produce NO can be those naturally occurring in the human body (nitrite, nitrate, nitrosothiols) or synthetic NO donors such as S-nitroso-N-acetylpenacillamine or related analogues) and S-nitrosoglutathione. Alternatively, endogenous precursors might be supplemented by systemic delivery of NO from donor drugs, including conventional organic nitrates (e.g. glyceryl trinitrate, isosorbide dinitrate, isosorbide mononitrate), or novel compounds such as diazeniumdiolates, syndnonimines, furoxans, and S-nitrosothiols, The materials can be formed of a single compound (e.g. just a copper (II) containing zeolite) or as mixtures of, for example, two components (e.g. a NO-loaded zeolite+copper oxide) to produce the desired NO release profiles. The materials can also be blended with, for example, polymers (such as polytetrafluoroethylene, polyurethane, silicones etc) to provide easier processing.

It is particularly preferred that the materials of the present invention are intended for use in medical applications including surgery and therapy, as well as in cosmetic application.

Thus, according to a further aspect of the present invention there is provided a pharmaceutical, neutraceutical or cosmetic preparation comprising a bifunctional material as described herein comprising irreversibly releasably adsorbed nitric oxide and being capable of catalytically producing nitric oxide from a suitable precursor molecule together with a pharmaceutical/neutraceutical/cosmetic carrier therefor.

The present invention also provides the use of a bifunctional material comprising irreversibly releasably adsorbed NO and being capable of catalytically producing NO from a suitable precursor molecule in the preparation of a medicament for use in the treatment or prophylaxis of disease.

Diseases or medical conditions which may be treated include infections of the skin, including dermatophyte fungi, leishmaniasis, molluscum and papilloma virus, and *mycobacterium* infections, including those associated with chronic circulatory disorders (e.g. diabetic foot ulcers). Further uses include therapeutic applications in anti-neoplastic activities, immune response modification, treatment of Raynaud's disease, wound healing and skin pigment modification. Yet further uses include treatment of restenonsis, psoriasis and eczema, and skin cancer (melanoma). Therapies for other bacterial problems include the reduction of severe foot or body odour problems, and in the treatment of Methicillin Resistant *Staphylococcus Aureus* infections.

An area of considerable potential with respect to the invention is the coating of or incorporation into medical devices that contact blood. Such items include medical instruments, cannulae (arterial and venous), catheters (e.g. urinary and those used in cardiology and surgical procedures), stents (e.g. coronary), shunts, prosthetic grafts and extracorporeal tubing, filters and associated components used in, for example, bypass surgery, renal dialysis and constant glucose monitoring equipment and insulin delivery pumps used in diabetes.

According to a further aspect of the present invention there is provided a medical article comprising a material according to the present invention which comprises irreversibly releasable absorbed nitric oxide and being capable of catalytically producing nitric oxide from a suitable precursor molecule.

The material of the medical article may be provided without NO loaded therein to allow loading with NO prior to use and/or storage of the medical device ready for subsequent use.

Alternatively, the material of the medical article may be provided as a zeolite material comprising releasably adsorbed NO.

Suitable medical articles for use in the present invention include stents, shunts, catheters, cannulae, extra-corporeal tubing, filters, wound dressings, bandages, self-adhesive plasters and patches.

The beneficial properties of NO may be advantageously employed in cosmetic and personal hygiene applications.

According to a further aspect of the present invention, there is provided use of a bifunctional material comprising releasably adsorbed NO and being capable of catalytically producing NO from a suitable precursor molecule in cosmetic and/or personal hygiene applications.

For example the materials of the present invention may be used in cosmetic preparations; deodorants; skin preparations such as anti-aging skin preparations and preparations applied before, during or after hair removal by shaving or by application of depilatory preparations; hair preparations; depilatory preparations and the like.

Accordingly, the present invention also provides, a cosmetic and/or personal hygiene product comprising a material according to the present invention.

The present invention also provides, as a further aspect, a method of releasing and producing NO comprising the steps of (iii) providing a material comprising irreversibly releasably adsorbed nitric oxide and being capable of catalytically producing NO from a suitable precursor molecule;

(iv) contacting said material with a medium into which said NO is to be provided, by release of the stored NO and by catalytic production of NO;

Such release of NO is preferably achieved in a controlled manner, for example, by providing a suitable material with an established controlled release profile. For example, the material may provide an initial stored burst of NO from the releasably stored NO, followed by a prolonged production of NO.

The medium into which the NO is to be released may be simply air surrounding the material or may be, for example, an aqueous medium.

The release may be performed either inside an animal body, topically to an animal body or in non-body applications such as release into cell cultures.

The release may be performed at any suitable temperature, however room or body temperature is preferred.

The method of releasing NO may be applied to the treatment of humans or animals and accordingly the present invention further provides as a further aspect a method of treatment or prophylaxis of an individual in need thereof comprising providing a material comprising releasably adsorbed nitric oxide and being capable of catalytically producing nitric oxide from a suitable precursor molecule and contacting said zeolite with said individual.

EXAMPLES

Example 1

Cu-Containing MFI Zeolite to Produce NO Catalytically from Nitrite

Figure 2:
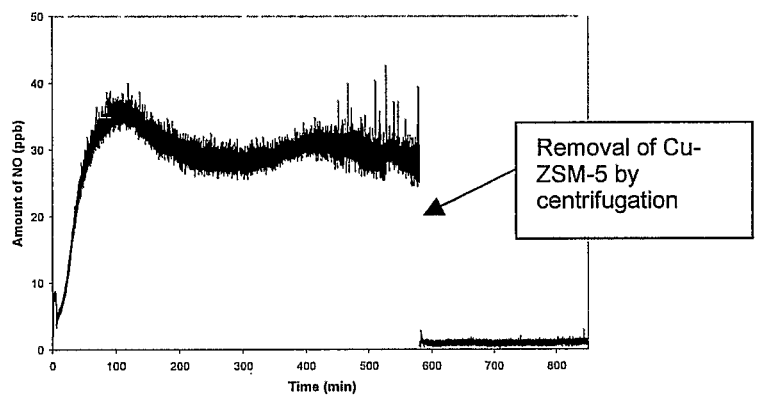
FIG. 2 shows the addition of nitrite and cysteine solution (at 5 mins) to a buffered solution in which solid Cu-MFI has been dispersed leads to a significant amount of NO being detected. Removal of the Cu-WI by centrifugation after 580 mins completely inhibits the production of NO, indicating that the activity is not due to leached copper.

Samples of copper (II)-exchanged MFI materials were prepared using standard synthesis and ion exchange techniques (Robson H.& Lillerud, K. P., *Verified Syntheses of Zeolitic Materials*, 2nd Revised Edition International Zeolite Association, 2001; www.iza-synthesis.org). Copper ions, particularly $Cu^+$, have been shown by several workers to be suitable catalysts for the reduction of nitrite to NO, both in biological systems (such as the enzyme nitrite reductase) and in inorganic systems in solution. Nitrite is particularly attractive as it is a naturally occurring substrate in mammalian blood at reasonable (high nM) levels. We therefore tested the Cu-MFI for activity in this reaction using chemiluminescence to detect NO. On exposing a dispersion of the zeolite powder (0.0007 g) in buffer (MOPSO pH 7.3) to 25 μL of 0.05 M sodium nitrite a significant amount of NO was produced (FIG. 1). Addition of a reducing agent (cysteine, 0.25 mL, $5 \times 10^{-4}$ M) to the solution increased the amount of NO formed considerably (up to ~ten fold), confirming that the active copper species in the zeolite is likely to be $Cu^+$, in agreement with previous studies of the mechanism of nitrite reduction. Leaching of copper out of the zeolite into solution can be ruled out as a significant source of catalysis by removal of the zeolite from the sample using a centrifuge and confirmation that the solution itself produced no further NO on addition of nitrite (FIG. 2).

0.0007 g of Cu-MFI was put in a sealed vial containing 2.6_ml of buffer (MOPSO pH=7.3). Nitrogen was bubbled through the solution for at least 2 min before the beginning of the experiment to remove all oxygen. 25 μL of $NaNO_2$ 0.05M were added (producing the first increase in the production of NO) followed by 0.25 mL of cysteine $5.10^{-4}$M. Due to some liquid evaporation that often occurs for long time measurement, the curve is fluctuating after 450 min. 211 μmole of NO were produced per gram of Cu-MFI, with a conversion rate of 11.8% for 580 min.

After measurement, the sample was put in a glass tube KIMAX® (Aldrich) and centrifuged for 1 h 30 min at 6000 rpm. Then, the supernatant was extracted and centrifuged again 1 h 30 min. This process was repeated again 2 times (at the end 4×1 h 30=6 h of centrifugation). Finally, the sample was put in a sealed vial and measured again (new addition of $NaNO_2$ and RSH (cysteine)).

Example 2

Bifunctional NO Storage and NO Catalytic Production by Cu-MFI

Figure 3:
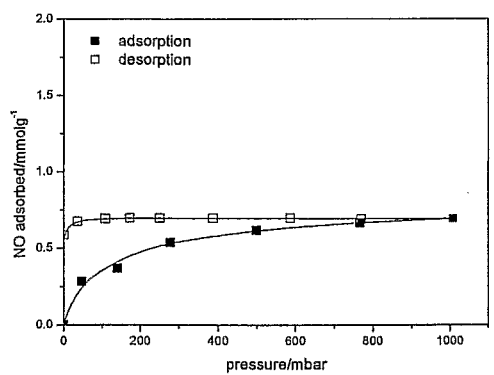
FIG. 3 shows the room temperature NO adsorption/desorption isotherm for dehydrated Cu-MFI indicating the strong hysteresis present between the adsorption and desorption arms of the isotherm.
Figure 4:
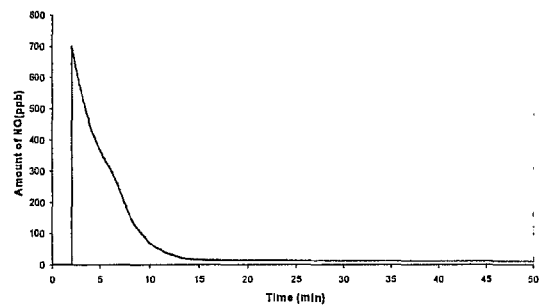
FIG. 4 shows the NO release profile for NO-loaded Cu-MFI on contact with a nucleophile containing medium (water or a buffer).
Figure 5:
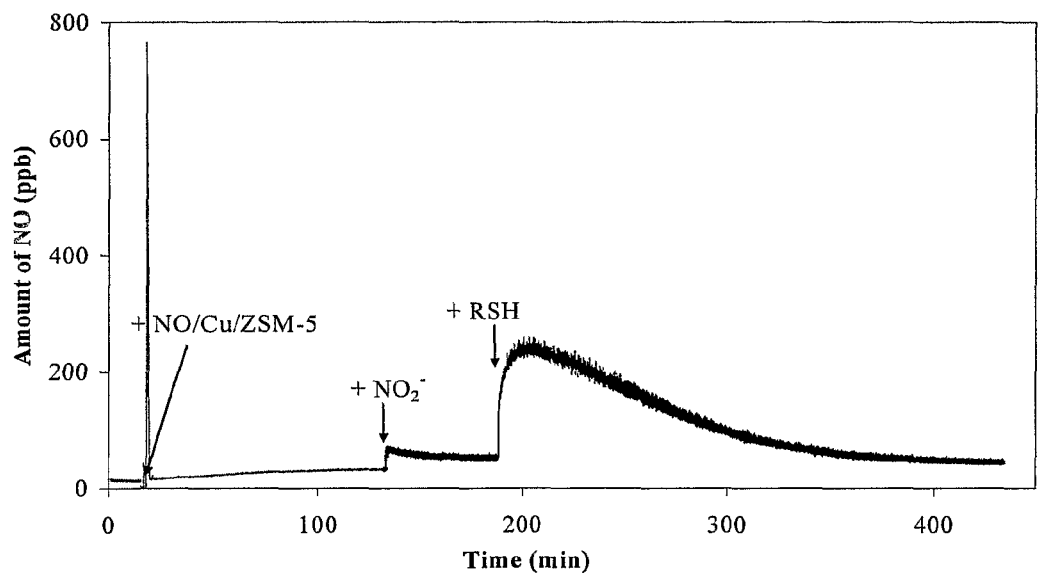
FIG. 5 shows the NO release profile of the stored NO in Cu-MFI (first peak at ~10 minutes) followed by addition of nitrite ($NO_2^-$) to the solution after ~130 mins, with significant production of NO, and subsequent addition of a reductant (cysteine, RSH) at around 180 mins.

A sample of copper (II) exchanged zeolite was prepared as in Example 1. FIG. 3 shows the adsorption/desorption isotherm for NO on Cu-ZSM-5 at room temperature, showing the hysteresis on desorption that makes for suitable gas storage materials. Room temperature infra red spectroscopy measurements of NO on Cu-MFI indicate that any copper dinitrosyls formed are slowly transformed into copper-complexed nitrite ($NO_2^-$) ions and so not all the adsorbed NO is available for release (M. C. Frost, M. M. Reynolds, M. E. Meyerhoff, *Biomaterials* 26, 1685 (2005)). On storage, the nitrogen containing species are mostly NO, which is available for release, together with nitrite, which is potentially available for transformation back into NO. Chemiluminescence measurements of the NO released by this material on contact with water (in the form of a buffer) confirm that the releasable NO storage capacity of Cu-MFI (1-2 μmol of NO per g of zeolite) is considerably less NO than that adsorbed initially (FIG. 4), which is consistent with the findings from IR (18). To the sample of Cu-MFI now dispersed in buffer an aliquot of nitrite anion was added (using the same method as described in example 1). Once again a significant amount of NO was produced indicating that Cu-MFI is a bifunctional material that can both store and catalytically produce NO. The act of storing NO does not affect the material's ability to catalytically produce NO (FIG. 5).

The buffer was first introduced in the sealed vial and nitrogen was bubbled through the solution for 2 minutes and measured so as to have a baseline (red curve). Then the vial opened, 0.019 g of Cu-MFI was introduced as quick as possible (green curve) and the vial sealed again. Nitrogen was still bubbled through the solution during the experiment. Cu-MFI stored with NO released $1,4.10^{-6}$ mol of NO/g of Cu-MFI. After 130 min, 25 μL of $NaNO_2$ 0.05M were added (blue curve, first increase) followed (180 min) by the addition of 0.25 mL of RSH $5.10^{-4}$M (blue curve, second increase). A high amount of catalytic NO was produced: 13.1 μmol/g of Cu-MFI with a conversion rate of 20.3% for 300 min. It should be noticed that a part of what is called "catalytic NO" can also be associated with the NO delivery coming from NO storage within Cu-MFI and hence the conversion rate has to be carefully considered.

Example 3

Catalytic NO Production Using $Cu_2O$ from Nitrite

Figure 6:
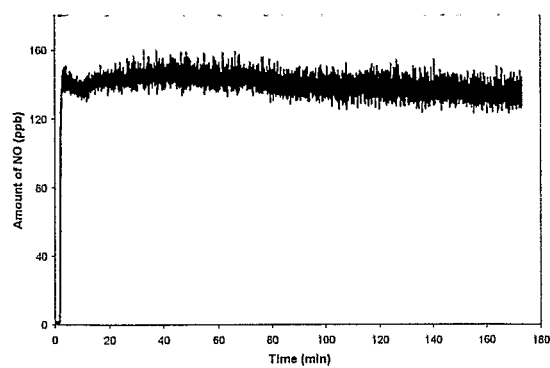
FIG. 6 shows that the addition of nitrite to a dispersion of $Cu_2O$ in buffer produces a large amount of NO, which is effectively constant over 180 mins.

The increase in NO production on addition of a reductant to the zeolites indicates that the active cation could be Cu+. Copper (I) oxide ($Cu_2O$) contains only Cu+. On exposing a dispersion of $Cu_2O$ the powder in buffer (MOPSO pH 7.3) to 25 μL of 0.05 M sodium nitrite a significant amount of NO was produced (FIG. 6). The amount of NO produced is effectively constant over 3 hours and shows no sign of decreasing. Note no reductant is required for this to reaction to occur.

$Cu_2O$ (0.0010 g) was weighed in the vial. When the vial was sealed, 2.6 mL of buffer (MOPSO) were added and nitrogen was bubbled through the solution for 2 min. Then, 25 μL of $NaNO_2$ 0.05M were added. Around 61 μmol of NO/g of $Cu_2O$ were produced with a conversion rate of 4.9% for 175 min.

Example 4

A Bifunctional Mixture of a NO-Storing Zeolite Combined with NO Production from Nitrite Using $Cu_2O$ Other zeolites, particularly those based on zeolite-A have very high capacity for NO storage. A mixture of such a material with copper (I) oxide has the potential to release stored NO plus produce NO catalytically from nitrite.

Figure 7:
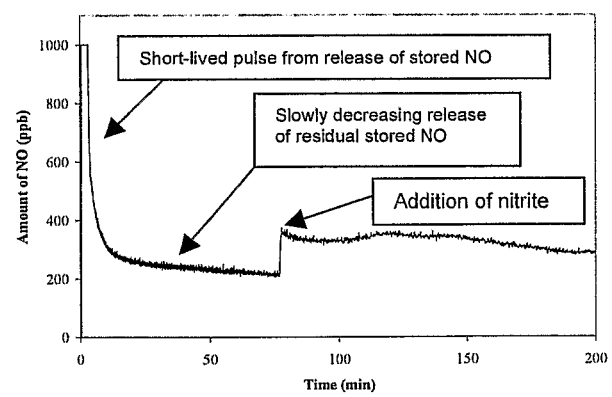
FIG. 7 shows a bifunctional mixture of a NO-storing zeolite combined with NO production from nitrite using $Cu_2O$. The stored NO is released from the Zn-LTA: a minimum (due to the precision loss) of 115 μmol of NO per gram of Zn-LTA were obtained. Using Zn-LTA instead of Cu-MFI, increased the NO storage by a factor of 80. After 200 minutes the zeolite is still releasing a significant amount of NO, but addition of $NaNO_2$ (25 μL, 0.05M) increases the NO produced significantly. An increase of ppb.s was obtained during one hour which means a NO delivery of 27.6 μmol of NO per gram of $Cu_2O$.

A mix of Zn-LTA and copper (I) oxide was studied. A previous study made in this research group showed that Zn-LTA was able to store a higher quantity of nitric oxide which can counterbalance the small amount obtained with Cu/ZSM-5 while copper (I) oxide provided the active specie, copper (I). Results are presented in FIG. 7.

First, a measurement of copper (I) oxide (0.0021 g) in MOPSO buffer to define the baseline (red curve). Then, the sealed vial was opened and Zn-LTA stored with nitric oxide (0.0066 g) was introduced (green curve). Then the vial was sealed again. When a constant delivery of nitric oxide was obtained, nitrites and cysteine were added (blue curve). As the production of nitric oxide is high, the nitric oxide analyzer automatically changed the scale to low sensitivity. To avoid this, the analyzer was fixed to a high sensitivity, inducing a loss of precision (flat curve) for the highest values obtained with NO storage.

Example 5

In Situ Rechargeable Gas Storage Using Bifunctional Zeolites

Materials and Methods
Synthesis of Cu-FAU X:

In polyethylene bottles, sodium aluminate (46.423 g, 0.5663 mol, Riedel de Haën, Al as $Al_2O_3$ 50-56%, Na as $Na_2O$ 40-45% and Fe as $Fe_2O_3$ 0.05%), was added to distilled water (72.095 g, 4.005 mol). Then, sodium hydroxide (5.38 g, 0.1345 mol, Fisher Scientific, 99.56%, 40 g/mol) was introduced to adjust the sodium concentration in the batch. The mix was stirred until dissolution at 100° C. (using a heating plate with a temperature control). The resultant gel (23.853 g) was added to distilled water (145.718 g, 8.095 mol) and sodium hydroxide (14.099 g, 0.3525 mol), and mixed until dissolution. Finally, this gel was combined quickly with a sodium silicate solution (52.331 g, 0.2160 mol, Riedel de Haën, NaOH 10%, SiO2 27%, 242.23 g/mol, (d=1.39) and stirred for 30 minutes. The crystallization took place at 90° C. during 8 hours without stirring in autoclaves. The product was filtered and washed till the pH was below 10. The product (13.2898 g) was obtained with a yield of 75.3%.
Copper Exchange:

Copper nitrate (6.0453 g, 0.025 mol, Alfa Aesar 98%, 241.6 g/mol) was dissolved in distilled water (100 mL) in a conical flak equipped with a stirring bar. Then, 1 g of zeolite was added and both were stirred during 24 h at room temperature. The product was recovered by filtration and washed three times with distilled water to remove the metal precursor from the outer surface of the zeolite. Finally, the product was dried at room temperature.
Characterization of Cu-FAU X:

A Stoe diffractometer system (Bragg-Brentano assembly) combined with the Stoe WinX$^{POW}$ software were used. The sample was inserted in between two plastic films (one was coated with pure petroleum jelly from Vaseline®) which were inserted in the sample-holder. XRD showed that the synthesized compound was the one expected.

ICP (Argilent 7500a ICP-MS) was used to estimate the copper exchange within the zeolites as well as to check the Si/Al ratio. Cu FAU X was mixed with Teflon (1:4, pressed using a 13 mm die) so as to make pellets for laser ablation and measured under argon flow. The copper exchange equalled 49.2%.
Quantification of NO Release Using Chemiluminescence Experiments:

The buffer (2.6 mL, pH7.4, MOPSO) was placed in a sealed vial equipped with a stirring bar and nitrogen was bubbled trough the solution 10 minutes before starting the experiment. Then, Cu FAU X stored with NO was introduced quickly into the vial and the measurements started immediately. Note that Cu FAU X stored with NO was previously kept in a sealed glass ampoule. Usually, the NO release was monitored for at least 60 minutes and then nitrites were added. Experiments were recorded at room temperature (22° C.) with a gas flow rate of 175 mL/min.

Figure 8:
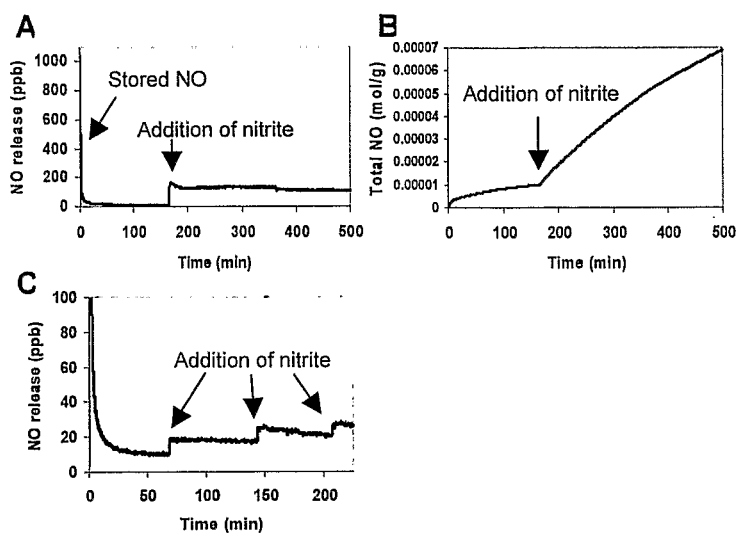
FIG. 8 (A) shows chemiluminescence measurements indicate that release of gas NO-loaded copper-exchanged zeolite-X is complete by ~150 minutes, but that the delivery of NO can be extended at a considerably enhanced flux by adding nitrite anions (25 μL, 0.05 M) to the solution. (B) The cumulative NO delivery profile for the experiment shown in FIG. 1A. (C) Addition of 25 μL of 0.005 M nitrite ions to the solution approximately matches the rate of release of residual stored NO at 60 minutes indicating that NO is delivered by both mechanisms simultaneously. Subsequent aliquots of added nitrite give rise to broadly similar increases in NO flux.

Extra-framework copper (II) ions are easily incorporated into zeolites, such as those with the zeolite-X (FAU) framework type, by standard ion exchange procedures, and such a material stores ~10 µmoles of deliverable NO per g of zeolite. The gas is released on contact with water with a relatively short-lived burst, followed by a steadily decreasing release of a small amount of NO that lasts for about 100-150 minutes. The lifetime of NO delivery is significantly extended at fluxes several orders of magnitude greater than needed for biological applications by adding 25 pL of 0.05 M nitrite ions to a simulated physiological fluid (2.6 mL, pH 7.4, $[NO_2^-]$=470 µM) in contact with the zeolite (FIGS. 8A and 8B). This delivers NO at an average rate of ~0.2 µmol per min per g of zeolite that lasts much longer than the release of any stored NO. The effect is not due to copper leaching from the zeolites, as removal of the solid by filtration completely inhibits the NO production. A nitrite concentration of 47 µM leads to NO production that approximately matches the release of stored NO at t=60 mins (~0.02 µmol min$^{-1}$, FIG. 8C). Subsequent additional aliquots of nitrite produce broadly similar increases in NO flux. This experiment indicates that NO is being delivered through both mechanisms simultaneously and that the amounts of NO produced are approximately additive. Nitrite concentrations as low as 1-5 µM lead to measurable NO fluxes, indicating that it may be possible to use endogenous nitrite as the substrate.

The most surprising feature of this work is that copper-exchanged zeolites are extremely well known for their ability to destroy NO in deNOx catalysis. That they can be used to produce NO in biologically relevant quantities goes against the traditional uses of copper-containing zeolites. The NO-producing reaction is also of significant mechanistic interest as no reducing agent was added to the system. It is known that Cu(I) is the most effective catalyst for NO production from nitrite (C. Frost, M. M. Reynolds, M. E. Meyerhoff, *Biomaterials* 26, 1685 (2005)). Dehydration followed by adsorption of NO produces some Cu(I) species in zeolites, and this is clearly enough to allow the significant transformation of nitrite to NO. Without the stored NO component very little Cu(I) is present, especially in the presence of water, and so no NO is produced on addition of nitrite. The NO pre-adsorption step reduces some Cu(II) to Cu(I) and allows the reaction to proceed.

This new concept in extended lifetime gas storage materials may be of use in biological applications. It might be extremely useful for applications such as anti-bacterial/anti-thrombotic coatings, where the initial burst of stored NO acts to kill bacteria quickly, preventing initial infection, while the slow production of NO from the zeolite prevents platelet activation and cell adhesion on contact with blood.

The invention claimed is:

1. A bifunctional zeolite comprising extra-framework copper cations, nitric oxide (NO) irreversibly releasably contained in the pores of the zeolite, and a NO precursor, where the bifunctional zeolite is capable of catalytically producing NO from the NO precursor.

2. The bifunctional zeolite of claim 1, wherein the copper cations are Cu(II) cations.

3. The bifunctional zeolite of claim 2, further comprising a reducing agent.

4. The bifunctional zeolite of claim 3, wherein the reducing agent is ascorbic acid or cysteine.

5. The bifunctional zeolite of claim 1, wherein the zeolite further comprises extra-framework metal cations selected from the group consisting of Li, Na, K, Ca, Mg, Fe, Mn, V, Ti, Ru, Rh, Co, Ni, Zn and Ag.

6. The bifunctional zeolite of claim 1, wherein the aluminosiliate framework of the zeolite further comprises a metal other than aluminum, additional positively charged ions, or anionic species.

7. The bifunctional zeolite of claim 6 wherein the anionic species are selected from the group consisting of $Cl^-$, $F^-$, $Br^-$, $I^-$, $OH^-$ and $SO_4^-$.

8. The bifunctional zeolite of claim 1, wherein the zeolite further comprises molecules within its pores, wherein the molecules are selected from the group consisting of water, solvent and a molecule derived from the components used in the manufacture of the zeolite.

9. The bifunctional zeolite of claim 1, sealed inside airtight packaging under a dry atmosphere.

10. The bifunctional zeolite of claim 1 wherein the NO precursor is selected from the group consisting of NO precursors that are naturally occurring in the human body, synthetic NO donors and S-nitrosoglutathione.

11. The bifunctional zeolite of claim 10, wherein the NO precursor is naturally occurring in the human body and is selected from a nitrite, a nitrate or a nitrosothiol compound.

12. The bifunctional zeolite of claim 10, wherein the NO precursor is S-nitroso-N-acetylpenacillamine.

13. The bifunctional zeolite of claim 1 blended with a polymer.

14. A pharmaceutical, nutraceutical or cosmetic preparation comprising the bifunctional zeolite of claim 1 together with a pharmaceutical/nutraceutical/cosmetic carrier therefor.

15. A medical article comprising a bifunctional zeolite according to claim 1.

16. The medical article of claim 15, wherein the article is selected from the group consisting of a stent, shunt, catheter, cannula, extra-corporeal tubing, filter, blood and insulin pump component, constant glucose monitoring tubing, wound dressing, bandage, self-adhesive plaster and patch.

17. A method of providing NO to a subject, the method comprising administering to the subject a bifunctional zeolite according to claim 1.

18. The method of claim 17, wherein the NO is provided for treating a skin condition caused by dermatophyte fungi, leishmaniasis, molluscum papilloma virus, or a *mycobacterium* infection.

19. A method of releasing and producing NO comprising contacting the bifunctional zeolite of claim 1 with a medium into which said NO is to be provided, the medium comprising a nucleophile effective to displace said NO, and, by virtue of said contacting, releasing the stored NO from the zeolite, and catalytically producing NO.

* * * * *